US012658324B2

(12) United States Patent
Kuo et al.

(10) Patent No.: US 12,658,324 B2
(45) Date of Patent: Jun. 16, 2026

(54) CARDIOVASCULAR DISEASE RISK ASSESSMENT SYSTEM AND CARDIOVASCULAR DISEASE RISK ASSESSMENT METHOD

(71) Applicant: China Medical University, Taichung City (TW)

(72) Inventors: Chin-Chi Kuo, Taichung City (TW); Sheng-Hsuan Chen, Taichung City (TW); Min-Yen Wu, Taichung City (TW)

(73) Assignee: China Medical University, Taichung City (TW)

( * ) Notice: Subject to any disclaimer, the term of this patent is extended or adjusted under 35 U.S.C. 154(b) by 0 days.

(21) Appl. No.: 19/043,842

(22) Filed: Feb. 3, 2025

(65) Prior Publication Data

US 2026/0066129 A1     Mar. 5, 2026

(30) Foreign Application Priority Data

Aug. 29, 2024    (TW) ................................. 113132719

(51) Int. Cl.
*G16H 50/30* (2018.01)
*A61B 6/00* (2006.01)
(Continued)

(52) U.S. Cl.
CPC ............. *G16H 50/30* (2018.01); *A61B 6/032* (2013.01); *A61B 6/503* (2013.01); *A61B 6/5217* (2013.01);
(Continued)

(58) Field of Classification Search
CPC ....... A61B 6/032; A61B 6/503; A61B 6/5217; G06T 7/0014; G06T 7/11;
(Continued)

(56) References Cited

U.S. PATENT DOCUMENTS

2021/0319900 A1    10/2021   Sharma et al.
2023/0005622 A1*    1/2023   Rabbat ................... G16H 50/30
2023/0289963 A1*    9/2023   Min ........................ A61B 5/055

FOREIGN PATENT DOCUMENTS

CN      116681659 A      9/2023
GB        2557263 A   *  6/2018   ............. G16H 50/30
TW      202349409 A     12/2023

OTHER PUBLICATIONS

Commandeur et al. "Fully Automated CT Quantification of Epicardial Adipose Tissue by Deep Learning: A Multicenter Study." Radiology: Artificial Intelligence. vol. 1, No. 6. https://doi.org/10.1148/ryai.2019190045 (Year: 2019).*

* cited by examiner

*Primary Examiner* — Linh Giang Le

(57) ABSTRACT
A cardiovascular disease risk assessment system includes a storage and a processor. The storage stores a plurality of reference medical images and a plurality of reference medical record data. The processor is signally connected to the storage and stores a program. The program includes a fat identification and quantification model and a risk assessment model, in which the fat identification and quantification model includes a CXR image extraction module and a CT image extraction module. The program estimates a cardiovascular disease incidence rate of a subject when the program is executed by the processor.

10 Claims, 12 Drawing Sheets

(51) Int. Cl.

| | |
|---|---|
| *A61B 6/03* | (2006.01) |
| *A61B 6/50* | (2024.01) |
| *G06T 7/00* | (2017.01) |
| *G06T 7/11* | (2017.01) |
| *G06V 10/26* | (2022.01) |
| *G06V 10/44* | (2022.01) |
| *G06V 10/54* | (2022.01) |
| *G06V 10/764* | (2022.01) |
| *G06V 10/82* | (2022.01) |
| *G16H 10/60* | (2018.01) |
| *G16H 30/40* | (2018.01) |

(52) U.S. Cl.

CPC .............. *G06T 7/0014* (2013.01); *G06T 7/11* (2017.01); *G06V 10/273* (2022.01); *G06V 10/44* (2022.01); *G06V 10/54* (2022.01); *G06V 10/764* (2022.01); *G06V 10/82* (2022.01); *G16H 10/60* (2018.01); *G16H 30/40* (2018.01); *G06T 2207/10016* (2013.01); *G06T 2207/10081* (2013.01); *G06T 2207/20084* (2013.01); *G06T 2207/20132* (2013.01); *G06T 2207/30012* (2013.01); *G06T 2207/30048* (2013.01); *G06T 2207/30061* (2013.01); *G06V 2201/031* (2022.01)

(58) Field of Classification Search

CPC . G06T 2207/10016; G06T 2207/10081; G06T 2207/20084; G06T 2207/20132; G06T 2207/30012; G06T 2207/30048; G06T 2207/30061; G06V 10/273; G06V 10/44; G06V 10/54; G06V 10/764; G06V 10/82; G06V 2201/031; G16H 10/60; G16H 30/40

See application file for complete search history.

410

T1
T2
T3
T4
T5
T6
T7
T8
T9
T10
T11
T12
L1

215

216
216
216
216

500

510   A target medical image and target medical record data of a subject are provided 520   Cardiovascular disease risk assessment system is provided 530   Fat identification and quantification step is performed 540   Risk assessment step is performed

CARDIOVASCULAR DISEASE RISK ASSESSMENT SYSTEM AND CARDIOVASCULAR DISEASE RISK ASSESSMENT METHOD

RELATED APPLICATIONS

This application claims priority to Taiwan Application Serial Number 113132719, filed Aug. 29, 2024, which is herein incorporated by reference.

BACKGROUND

Technical Field

The present disclosure relates to a medical information analysis system and a method thereof. More particularly, the present disclosure relates to a cardiovascular disease risk assessment system and a cardiovascular disease risk assessment method.

Description of Related Art

With the advent of the global aging era, the prevalence and number of age-related diseases such as cardiovascular disease and diabetes are also growing rapidly. As people age and the pressure of modern life increases, the cardiovascular disease incidence also increases. Complications of cardiovascular disease, including coronary syndrome, stroke and hypertensive heart disease, will have a huge impact on global medical care resources.

Previous studies have pointed out that the cardiovascular disease is highly correlated with obesity. Obese people usually have chronic inflammation throughout the body due to more fat in the body, and the cardiovascular disease is highly correlated with inflammation. The higher body mass index (BMI) combined with body fat, the higher inflammation index will be. Furthermore, excess fat will also affect the balance of endocrine secretion, especially the secretion of leptin and renin. High fat content will inhibit the secretion of leptin and activate the secretion of renin, causing water and sodium ion retention in the body, and leading to the risk of heart failure. In addition, excess fat can cause organ burden. For example, fat pressing outside the left atrium may increase the incidence of atrial fibrillation, and fat pressing outside the left ventricle may cause heart failure.

Therefore, analyzing the fat distribution in a body of a subject and the fat content around heart of the subject is crucial to find out the groups potentially at risk of the cardiovascular disease, so that medical resources can be invested early to reduce the incidence and severity of the cardiovascular disease. It will be of great clinical application value.

SUMMARY

According to one aspect of the present disclosure, a cardiovascular disease risk assessment system includes a storage and a processor. The storage stores a plurality of reference medical images and a plurality of reference medical record data, and each of the plurality of reference medical images corresponds to one of the plurality of reference medical record data, wherein each of the plurality of reference medical images is a reference CXR image and/or a reference CT image sequence, and the reference CT image sequence includes a plurality of reference cross-sectional CT images and/or a reference sagittal CT image.

The processor is signally connected to the storage and stores a program, wherein the program estimates a cardiovascular disease incidence rate of a subject when the program is executed by the processor. The program includes a fat identification and quantification model and a risk assessment model. The fat identification and quantification model is for calculating a probability of having an epicardial fat in each of the plurality of reference medical images or identifying a fat distribution and quantifying a fat content around heart in each of the plurality of reference medical images, and the fat identification and quantification model includes a CXR image extraction module and a CT image extraction module. The CXR image extraction module is for calculating the probability of having the epicardial fat in each of the plurality of reference CXR images. The CXR image extraction module is obtained by labelling each of the plurality of reference CXR images and then integrating with one of the plurality of reference medical record data corresponding, and then training to convergence by a two-dimensional CNN convolutional neural network learning classifier. The CT image extraction module is for identifying the fat distribution and quantifying the fat content around heart in each of the plurality of reference CT image sequences. The CT image extraction module identifies and segments an organ and a tissue in each of the plurality of reference CT image sequences by a three-dimensional U-net convolutional neural network classifier to obtain a plurality of reference segmented CT images, and analyzes a Hounsfield unit in each of the plurality of reference CT image sequences to obtain a plurality of fat contents by a feature model. The risk assessment model is for assessing the cardiovascular disease incidence rate in the subject after 1 to 5 years. The risk assessment model is obtained by integrating the probability of having the epicardial fat or the fat content around heart obtained by the fat identification and quantification model with one of the plurality of reference medical record data corresponding, and then training to convergence by a gradient descent algorithm.

According to another aspect of the present disclosure, a cardiovascular disease risk assessment method includes following steps. A target medical image and a target medical record data of a subject are provided, and the target medical image is a target CXR image and/or a target CT image sequence. The aforementioned cardiovascular disease risk assessment system is provided. A fat identification and quantification step is performed, wherein the CXR image extraction module of the fat identification and quantification model is used to calculate a probability of having an epicardial fat in the target CXR image, and the CT image extraction module of the fat identification and quantification model is used to identify a fat distribution in the target CT image sequence and quantify a fat content around heart in the target CT image sequence. A risk assessment step is performed, wherein the target medical record data is integrated with the probability of having the epicardial fat or the fat content around heart using the risk assessment model to calculate a cardiovascular disease incidence rate in the subject after 1 to 5 years.

BRIEF DESCRIPTION OF THE DRAWINGS

The present disclosure can be more fully understood by reading the following detailed description of the embodiment, with reference made to the accompanying drawings as follows.

DETAILED DESCRIPTION

Reference will now be made in detail to the present embodiments of the present disclosure, examples of which are illustrated in the accompanying drawings.

I. Cardiovascular Disease Risk Assessment System

Figure 1:
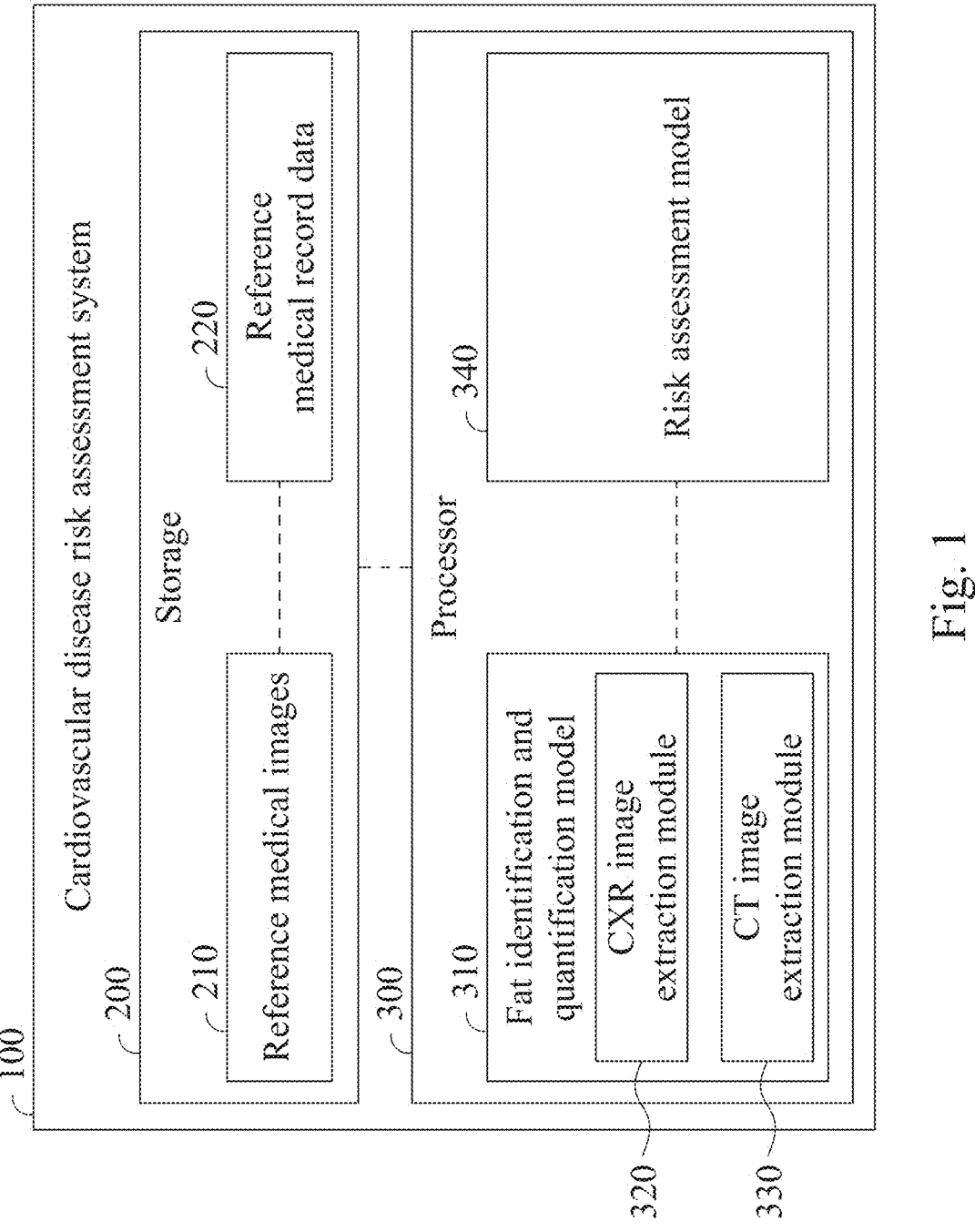
FIG. 1 is a structural schematic view of a cardiovascular disease risk assessment system according to one embodiment of the present disclosure.
Figure 3B:
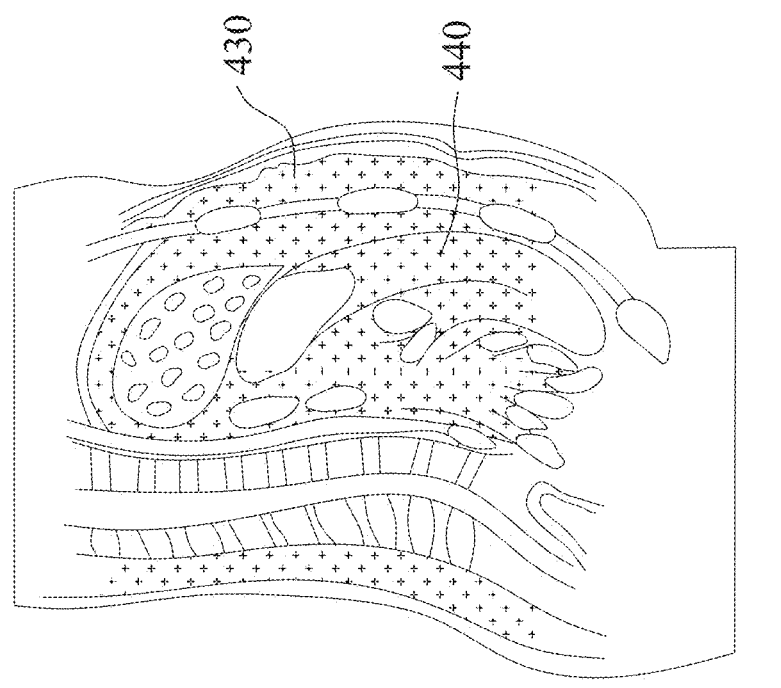
FIG. 3A and FIG. 3B are schematic diagrams showing the distribution of the cardiac fat and the abdominal fat, respectively.
Figure 3A:
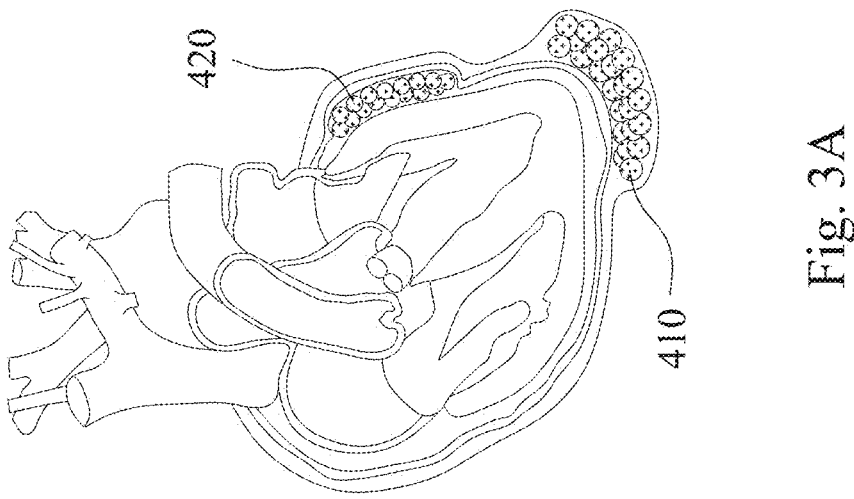
Figure 4A:
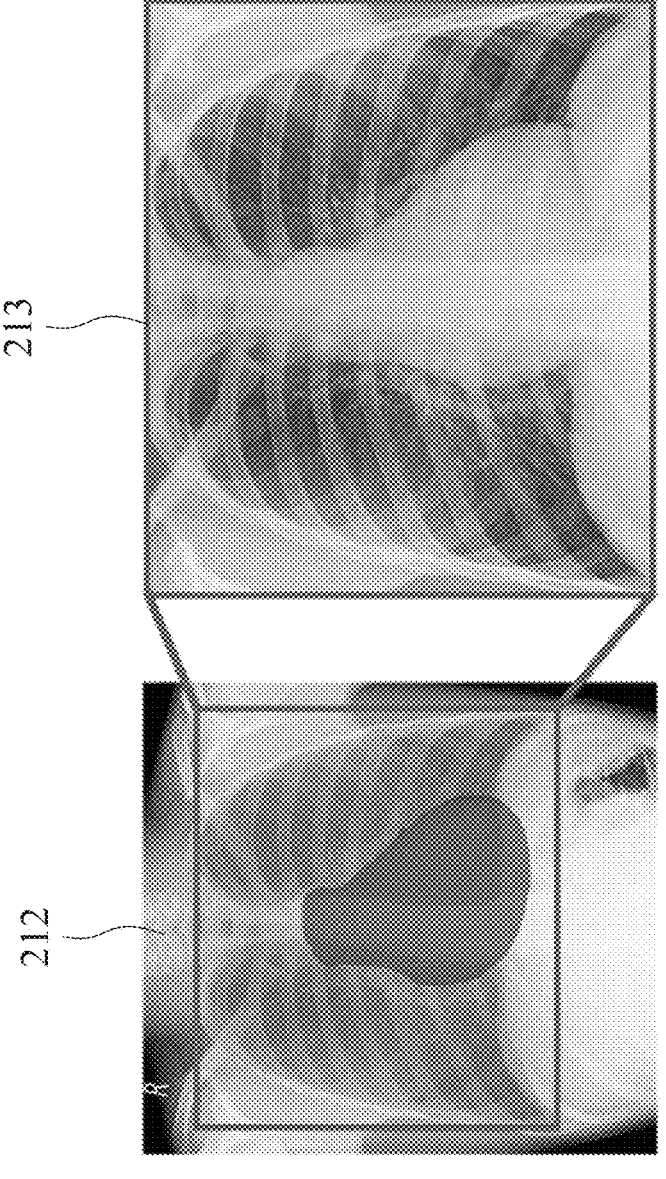
FIG. 4A, FIG. 4B and FIG. 4C show output results after processing by the CXR image extraction module.
Figure 4C:
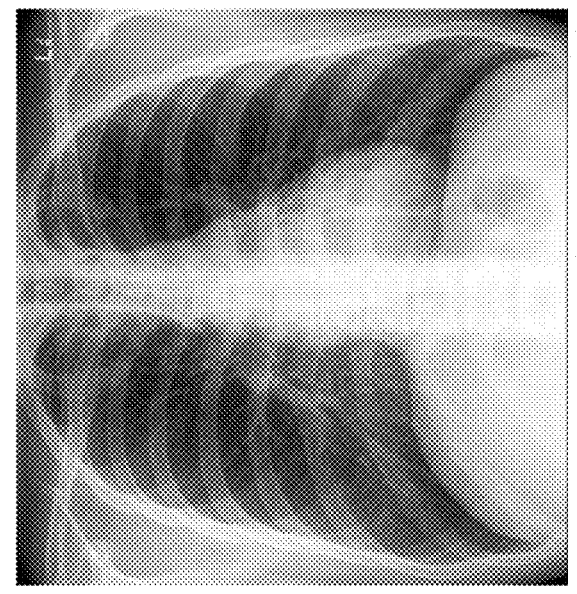
Figure 4B:
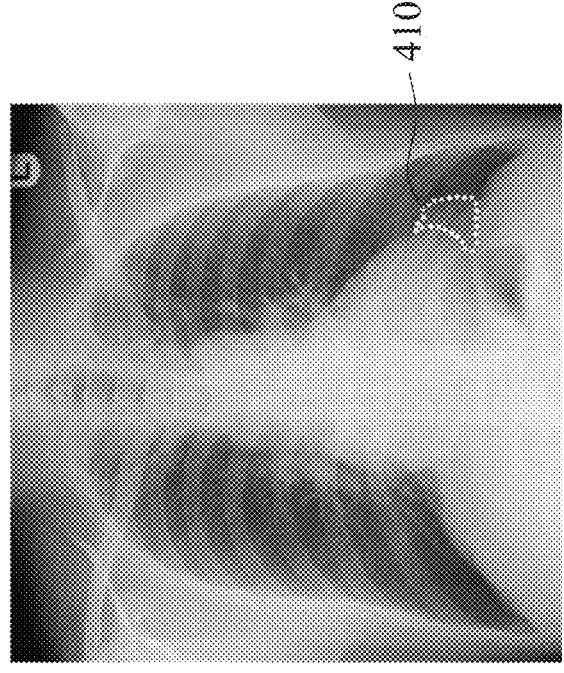
Figure 5B:
FIG. 5A and FIG. 5B are the reference sagittal CT image and the reference cross-sectional CT image of different imaging planes, respectively.
Figure 5A:
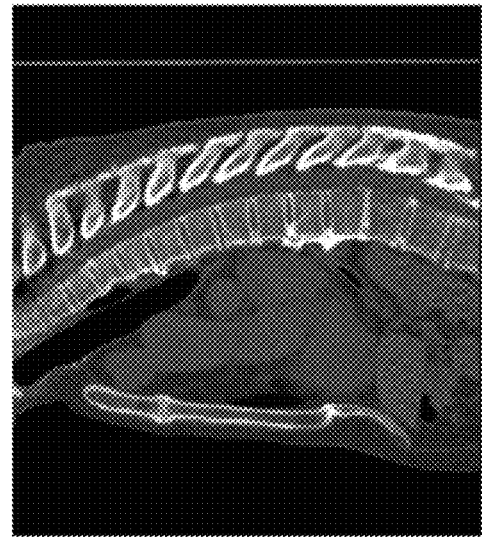
Figure 5C:
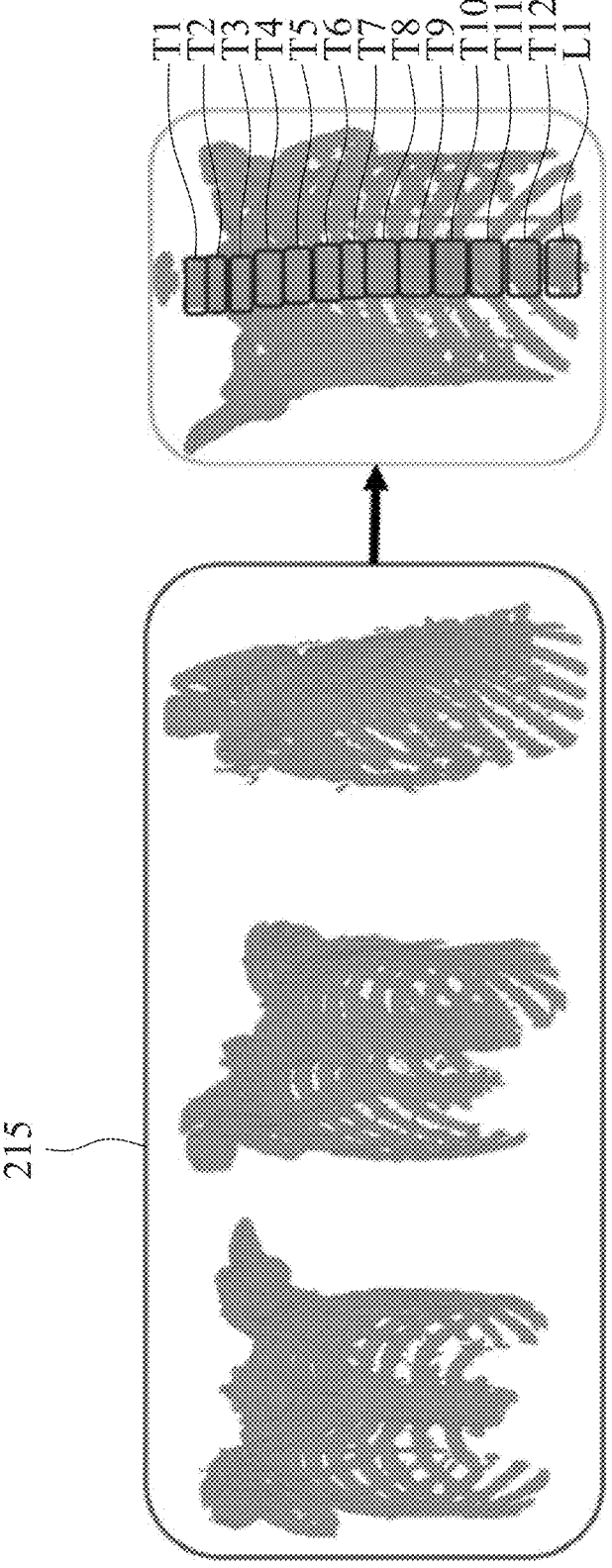
FIG. 5C, FIG. 5D and FIG. 5E show output results after processing by the CT image extraction module.
Figure 5D:
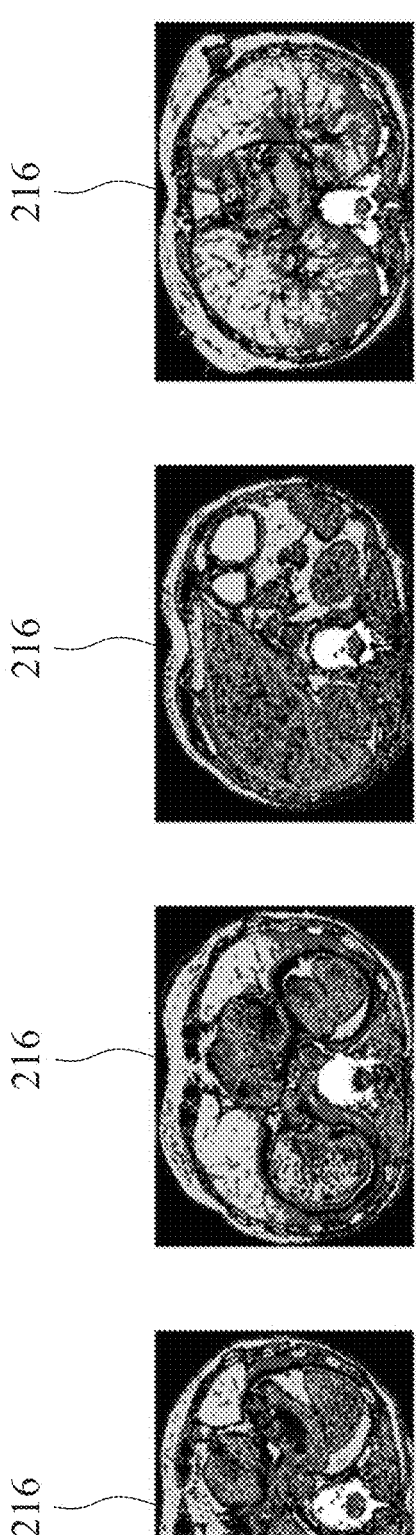
Figure 5E:
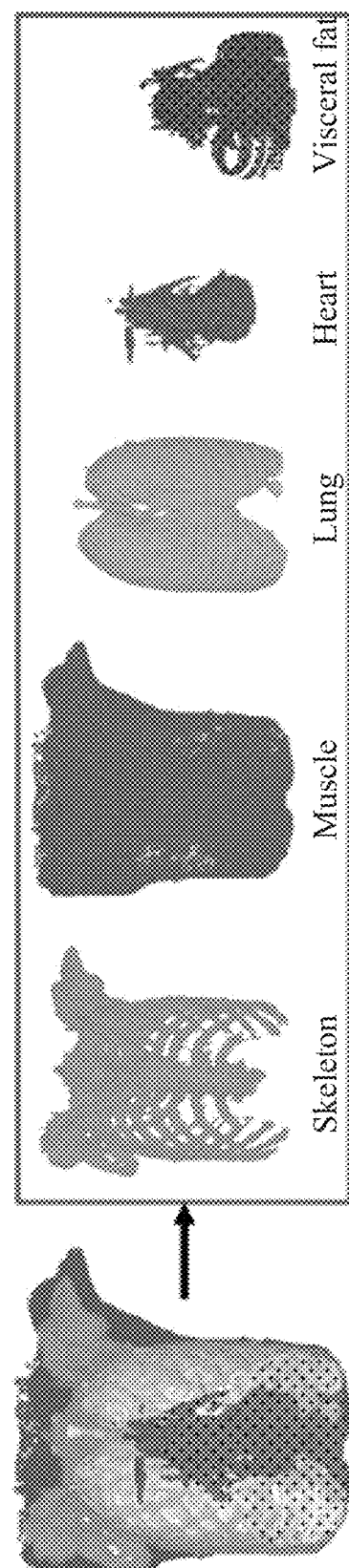

Reference is made to FIG. 1 to FIG. 5E. FIG. 1 is a structural schematic view of a cardiovascular disease risk assessment system 100 according to one embodiment of the present disclosure. FIG. 2A is a structural schematic view of a two-dimensional CNN convolutional neural network learning classifier of a CXR image extraction module 320. FIG. 2B is a structural schematic view of a three-dimensional U-net convolutional neural network classifier of a CT image extraction module 330. FIG. 2C is a structural schematic view of the CXR image extraction module 320 of the cardiovascular disease risk assessment system 100. FIG. 2D is a structural schematic view of the CT image extraction module 330 of the cardiovascular disease risk assessment system 100. FIG. 3A is a schematic diagram showing the distribution of the cardiac fat. FIG. 3B is a schematic diagram showing the distribution of the abdominal fat. FIG. 4A, FIG. 4B and FIG. 4C show output results after processing by the CXR image extraction module 320. FIG. 5A and FIG. 5B are the reference sagittal CT image and the reference cross-sectional CT image of different imaging planes, respectively. FIG. 5C, FIG. 5D and FIG. 5E show output results after processing by the CT image extraction module 330.

As shown in FIG. 1, the cardiovascular disease risk assessment system 100 includes a storage 200 and a processor 300. The storage 200 stores a plurality of reference medical images 210 and a plurality of reference medical record data 220, and each of the reference medical images 210 corresponds to one of the reference medical record data 220. Each of reference medical images 210 is a reference CXR (chest x-ray) image 211 and/or a reference CT (computerized tomography) image sequence 214, and the reference CT image sequence 214 includes a plurality of reference cross-sectional CT images and/or a reference sagittal CT image.

The processor 300 is signally connected to the storage 200 and stores a program (not shown), wherein the program estimates a cardiovascular disease incidence rate of a subject when the program is executed by the processor 300. The program includes a fat identification and quantification model 310 and a risk assessment model 340.

The fat identification and quantification model 310 is for calculating a probability of having an epicardial fat 410 in each of the reference medical images 210 or identifying a fat distribution and quantifying a fat content around heart in each of the reference medical images 210, and the fat identification and quantification model 310 includes a CXR image extraction module 320 and a CT image extraction module 330.

The CXR image extraction module 320 is for calculating the probability of having the epicardial fat 410 in each of the reference CXR images 211. The CXR image extraction module 320 is obtained by labelling each of the reference CXR images 211 and then integrating with one of the reference medical record data 220 corresponding, and then training to convergence by a two-dimensional CNN convolutional neural network learning classifier. Please further refer to FIG. 2A, which is the structural schematic view of the two-dimensional CNN convolutional neural network learning classifier of the CXR image extraction module 320.

The CT image extraction module 330 is for identifying the fat distribution in each of the CT image sequences 214 and quantifying the fat content around heart in each of the CT image sequences 214. The CT image extraction module 330 identifies and segments an organ and a tissue in each of the reference CT image sequences 214 by a three-dimensional U-net convolutional neural network classifier to obtain a plurality of reference segmented CT images 216, and analyzes a Hounsfield unit in each of the reference CT image sequences 214 to obtain a plurality of fat contents by a feature model. Please further refer to FIG. 2B, which is the structural schematic view of the three-dimensional U-net convolutional neural network classifier of the CT image extraction module 330.

In detail, in the CT image extraction module 330, pre-labeled images are used to train the three-dimensional U-net convolutional neural network classifier until it converges, so that the three-dimensional U-net convolutional neural network classifier can subsequently be used for organ recognition. The feature model is built using conventional image processing technology to assist the three-dimensional U-net convolutional neural network classifier in segmenting organs in the reference CT image sequences 214, and is used to identify non-fixed-shaped tissues around the organs, such as fat, blood, and tissue fluid. Furthermore, mathematical morphology combined with methods such as geometric figures, digital signals and anomaly detection are used in the feature model to filter original of the reference CT image sequences 214 by the Hounsfield unit value thereof, and each expected tissue density can be obtained. The obtained tissue density is combined with the anatomical content to recognize the organs of each corresponding tissue in the corresponding position of the body. For example, the muscle tissue between the two lung lobes is most likely to be in the heart area, and the organ at the lower edge of the lung lobes where muscle, blood, and fat each account for a certain proportion is the liver. Then the proportion of fat around the organ is further calculated.

Fat can be identified by the fat identification and quantification model 310 includes the cardiac fat and the abdominal fat. As shown in FIG. 3A, the periphery of the heart has a conical double-layered fibroserosal pericardium, which surrounds the heart and the roots of the great blood vessels entering and exiting the heart, and contains an inner serous pericardium and an outer fibrous pericardium. Heart fat can be divided into the epicardial fat 410 and the pericardial fat 420 according to distribution location. The epicardial fat 410 is the adipose tissue attached between the outer fibrous pericardium and the heart, and the pericardial fat 420 is the adipose tissue attached between the inner serous pericardium and the heart. Previous studies have pointed out that the epicardial fat 410 and the pericardial fat 420 are positively associated with cardiovascular disease, vascular calcification, and regional inflammation. As shown in FIG. 3B, abdominal fat can be divided into the subcutaneous fat 430 and the visceral fat 440 according to distribution location. The subcutaneous fat 430 is the adipose tissue attached under the skin, and visceral fat 440 is the adipose tissue attached to the mesentery around the abdomen and gastro-intestinal tract. The visceral fat 440 is closely related to the incidence rate of arteriosclerosis, hypertension, diabetes, hyperlipidemia and cardiovascular disease.

The CXR image is easy to obtain and the shooting cost thereof is low, but the amount of information that the CXR image can provide is often underestimated. Therefore, the CXR image extraction module 320 focuses on extracting more subject-related information from the CXR image. Since most CXR images do not capture the entire abdominal range, and the contrast of the myocardium in the CXR image is higher than that of fat, it is difficult to identify the fat within the myocardium, so the CXR image is only used to analyze the epicardial fat 410. In addition, although CT image sequences have high resolution to examine the status of subjects, the fluid content in the body, such as the fat content around heart and the visceral fat content, is often not easy to quantify. Therefore, a computer vision technology is used in the CT image extraction module 330 to quantify the fat content around organs and the CT image extraction module 330 can extract the epicardial fat 410, the pericardial fat 420, the subcutaneous fat 430 and the visceral fat 440 according to the imaging range.

Figure 2A:
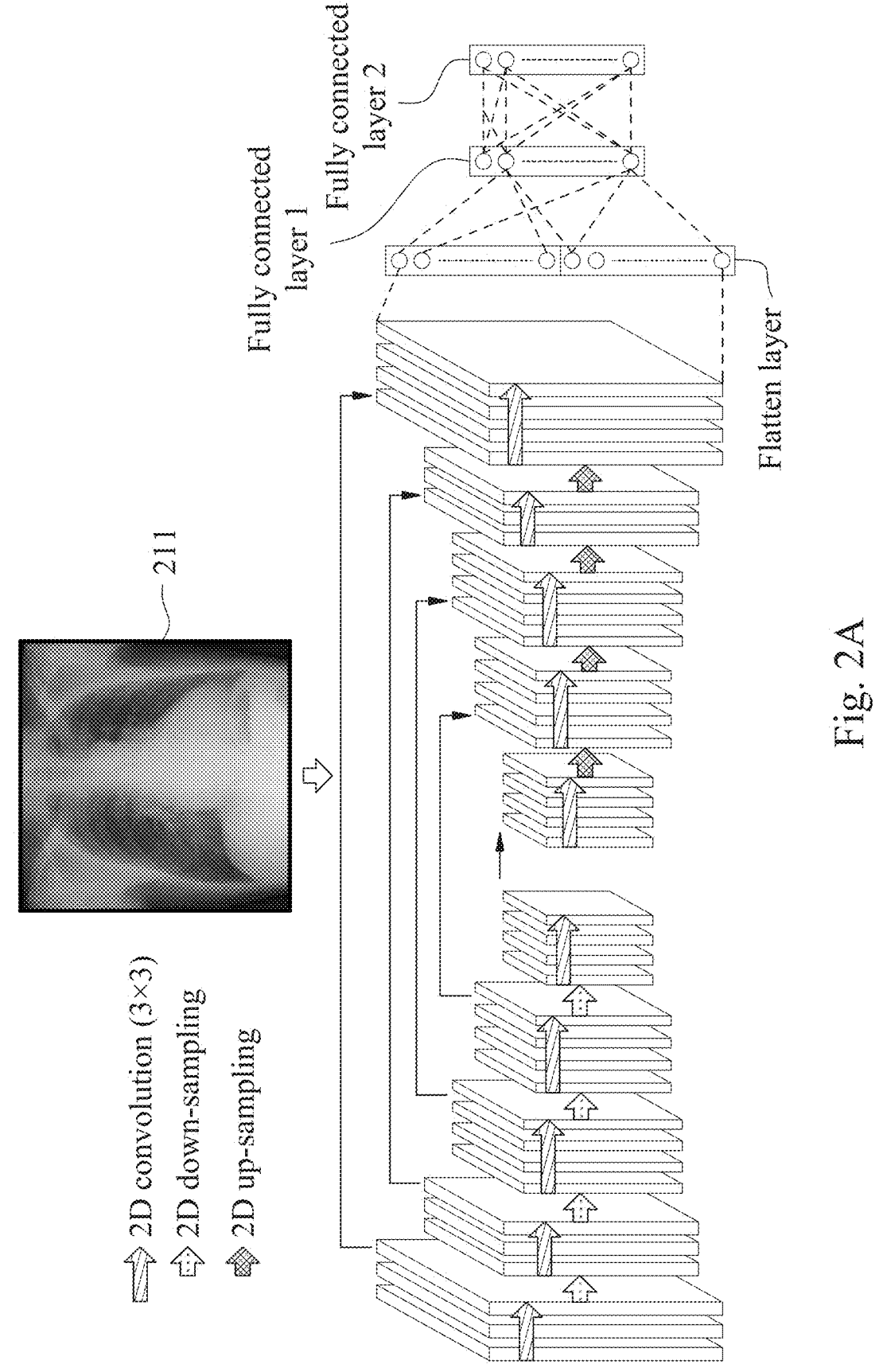
FIG. 2A is a structural schematic view of a two-dimensional CNN convolutional neural network learning classifier of a CXR image extraction module.
Figure 2B:
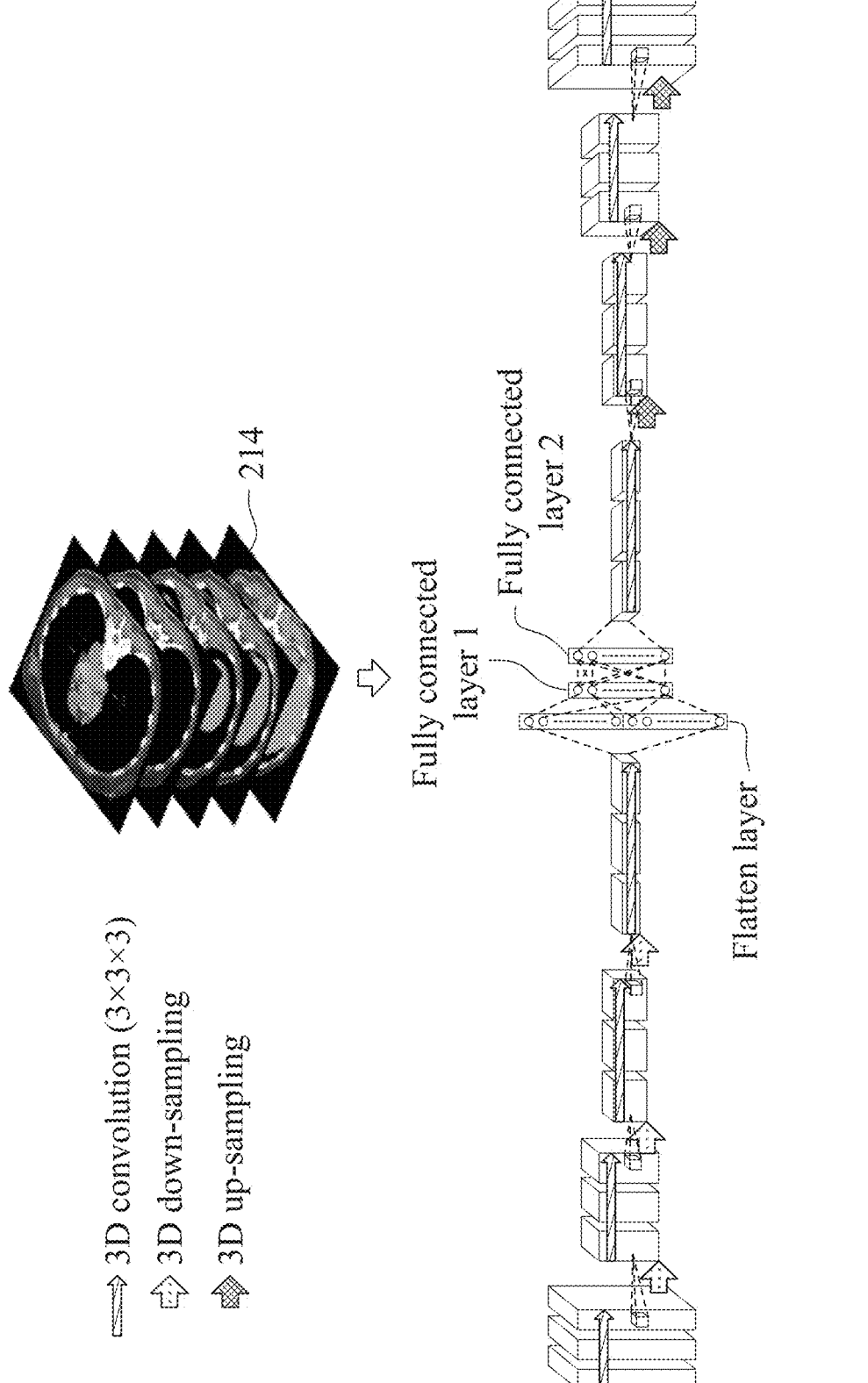
FIG. 2B is a structural schematic view of a three-dimensional U-net convolutional neural network classifier of a CT image extraction module.
Figure 2D:
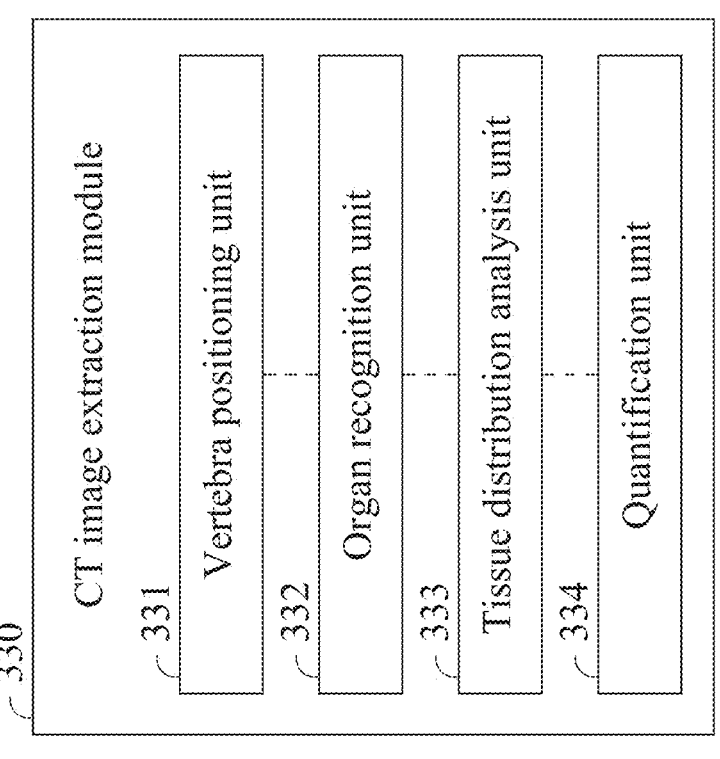
FIG. 2C and FIG. 2D are structural schematic views of the CXR image extraction module and the CT image extraction module of the cardiovascular disease risk assessment system, respectively.
Figure 2C:
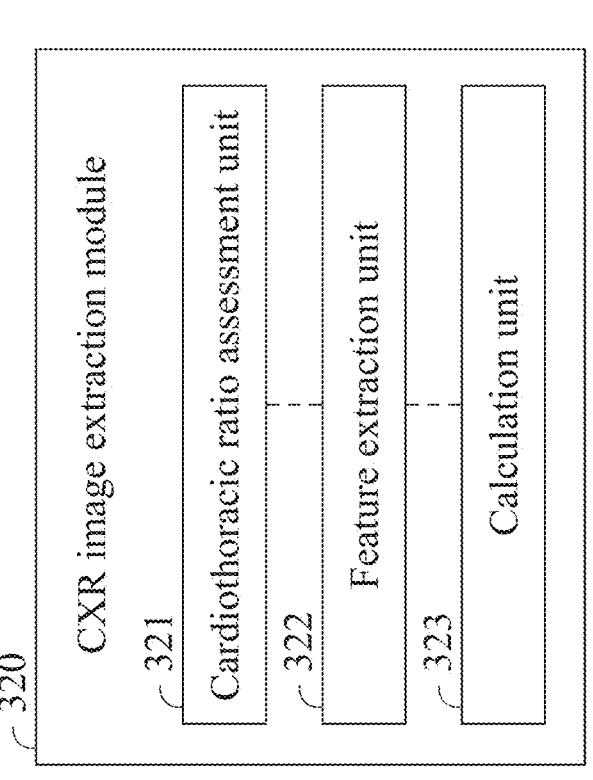

Furthermore, please refer to FIG. 2C and FIG. 4A to FIG. 4C. As shown in FIG. 2C, the CXR image extraction module 320 can include a cardiothoracic ratio assessment unit 321, a feature extraction unit 322, and a calculation unit 323.

The cardiothoracic ratio assessment unit 321 is for identifying and segmenting a lung lobe contour and a heart contour in each of the reference CXR images 211 to output a plurality of reference segmented CXR images 212. In detail, the reference CXR images 211 can be labeled by experts first, and subjects who have undergone both CT angiography and CXR angiography in the same year can be screened out. Image processing technology can be used to identify the characteristics of the epicardial fat 410 in each of the reference CT image sequences 214, which can be used as the basis for pre-labeling the reference CXR images 211, and then confirmed by experts to reduce a large amount of labeling time. Then the lung lobe contour and the heart contour in each of the reference CXR images 211 labeled is segmented to obtain a plurality of reference segmented CXR images 212.

The CXR image extraction module 320 can further include a cropping unit (not shown) for removing unnecessary image ranges around the heart and a lung lobe in the reference segmented CXR images 212 to obtain a plurality of reference cropped segmented CXR images 213, thereby increasing the accuracy of the CXR image extraction module 320.

The feature extraction unit 322 is for detecting and locating an edge, a texture and a shape of a heart and the epicardial fat 410 in each of reference segmented CXR images 212 to output a plurality of reference labeled CXR images.

The calculation unit 323 is for calculating the probability of having the epicardial fat in each of the reference labeled CXR images. The calculation unit 323 is connected to the fully connected layer of the feature extraction unit 322, and the two-dimensional CNN convolutional neural network learning classifier is used to calculate the probability of having the epicardial fat 410 in the reference labeled CXR image.

Please refer to FIG. 4B and FIG. 4C, which show final output results after processing by the CXR image extraction module 320. FIG. 4B is a reference CXR image 211 of a heart with the epicardial fat 410, and FIG. 4C is a reference CXR image 211 of a healthy heart. Compared to FIG. 4C, it can be observed that there is an extended area at the lower edge of the heart contour in FIG. 4B, which is the epicardial fat 410.

Furthermore, please refer to FIG. 2D and FIG. 5A to FIG. 5E. As shown in FIG. 2D, the CT image extraction module 330 can include a vertebra positioning unit 331, an organ recognition unit 332, a tissue distribution analysis unit 333, and a quantification unit 334.

The reference CT image sequences 214 include continuous slice images along the body part, which have spatial continuity. If the images are analyzed independently, a lot of spatial information will be missing. Therefore, the three-dimensional U-net convolutional neural network classifier is used as the main method in the CT image extraction module 330 for tissue identification and segmentation. The three-dimensional U-net convolutional neural network classifier is an extension model of CNN and has the advantage of constructing a model with spatial continuity, so it can help capture the prototype contours of organs in the subject (such as the heart and kidneys), and can also help determine the location of adipose tissue such as the cardiac fat and the abdominal fat. Furthermore, since the deep learning model is not easy to distinguish individual differences between similar objects, such as how much fat a heart contains, the feature model is also used in the CT image extraction module 330 as an auxiliary analysis. The feature model uses methods such as mathematical morphology, geometric shapes, digital signals, and anomaly detection to identify and analyze differences between individuals, while measuring non-fixed-shaped tissues (such as fat, blood, and muscle) within the organ.

The vertebra positioning unit 331 is for stacking the reference cross-sectional CT images in each of the reference CT image sequences 214 into a three-dimensional space to output a plurality of reference three-dimensional CT images 215, and is for distinguishing a vertebra position in each of the reference three-dimensional CT images 215. Furthermore, in order to achieve fully automatic measurement of whole body tissues, the identification and positioning of vertebrae is a key step in the CT image extraction module 330. According to the gold standard for diagnosis of most diseases, the CT images of specific vertebrae positions are mostly used as the basis for diagnosis. Currently, the sagittal CT images are mostly used to analyze vertebral positioning. Reference is made to FIG. 5A and FIG. 5B. FIG. 5A is the reference sagittal CT image, and FIG. 5B is the reference cross-sectional CT image. As shown in FIG. 5A, it is easier to identify the complete contour of the vertebrae and the sternum in the reference sagittal CT image. However, compared with the reference sagittal CT image, the reference cross-sectional CT image is still easier to obtain. As shown in FIG. 5C, the vertebra positioning unit 331 stacks the reference cross-sectional CT images into the three-dimensional space to output the reference three-dimensional CT images 215, and then uses the reference three-dimensional CT images 215 to distinguish the positions of the vertebrae. However, CT does not always take pictures of fixed body regions. For example, an abdominal CT may take pictures from the upper abdomen to the pelvis, or from the neck to the lower abdomen. Therefore, it is necessary to identify the vertebrae characteristics of each segment to determine the corresponding positions of other vertebrae. For example, the T12 vertebra connects the terminal ribs, and the L5 vertebra aligns with the ilium.

The organ recognition unit 332 is for segmenting the organ and the tissue in each of the reference three-dimensional CT images 215 to output a plurality of reference segmented CT images 216. Further, as shown in FIG. 5D, the three-dimensional U-net convolutional neural network classifier is used in the organ recognition unit 332 to segment the organs and tissues in the reference three-dimensional CT images 215, including recognizing organs and tissues with small differences between individuals and relatively fixed positions, such as the heart, the liver, the kidneys, the lung lobes, and the bronchi, to output a plurality of reference segmented CT images 216. The reference segmented CT images 216 outputted by the organ recognition unit 332 are verified based on the reference three-dimensional CT images 215 outputted by the vertebra positioning unit 331, and can assist in correcting the results of the vertebra positioning unit 331. For example, the location of the kidneys should be between the T11 vertebrae and the L3 vertebrae.

The tissue distribution analysis unit 333 is for analyzing the Hounsfield unit in each of the reference CT image sequences 214 to obtain a tissue distribution in each of the reference CT image sequences 214, and measuring the fat contents in each of the reference CT image sequences 214. The fat contents can include an epicardial fat content, a fat content around heart and a visceral fat content. Further, as shown in FIG. 5E, the feature model is used in the tissue distribution analysis unit 333 to analyze the Hounsfield unit in the reference CT image sequences 214 for analyzing the composition distribution within each organ in the reference CT image sequences 214. In the analysis of non-fixed-shaped tissues such as fat, muscle and blood vessels, the feature model is also used as the measurement basis to measure information such as the epicardial fat content, the pericardial fat content and the visceral fat content. The above measurement value is the amount of image pixels in the three-dimensional space. Therefore, the tissue distribution analysis unit 333 uses the imaging parameters in the reference CT image sequences 214 to restore the image pixel value and the physical value in the actual space. For example, the width of each pixel value is 0.45 mm to achieve consistent data size.

The quantification unit 334 is for quantifying the fat contents in each of the reference CT image sequence 214 and one of the reference segmented CT images 216 corresponding with a fat profile index to obtain the fat content around heart. The fat profile index can include a fat/heart ratio quartile, a fat/heart ratio, and an actual fat size restoration. Further, the fat/heart ratio quartile is calculated by screening the reference segmented CT images 216 at 25%, 50% and 75% of the heart height range, and extracting the area ratio of the heart and the fat around heart. The fat/heart ratio is calculated by extracting the pixel ratio of the heart and the fat around heart in the whole heart range. The method for the actual fat size restoration is to select the reference segmented CT images 216 of the whole heart height range, extract the fat pixels around heart, and then convert the fat pixel value into the actual area size through the conversion ratio between the image and the actual space. By standardizing the above three fat profile indexes, the fat status of different individuals can be compared with each other, and can be used as normalized features required for subsequent training the risk assessment model 340.

In detail, the number of the CT image sequences taken by different individuals may be different. For example, if a computed tomography scan is performed with a slice thickness of 1 mm or a slice thickness of 5 mm, there will be 5 times difference in the number of the CT image sequences obtained. Therefore, in the heart range, the ratio of heart tissue to fat tissue between images is averaged for normalization to eliminate the differences caused by the number of images. In addition, the normalization can also perform volumetric conversion of the actual space through the image restoration ratio (Pixel Spacing Attribute) retained when taking the CT image sequence. For example, Pixel Spacing Attribute=(0.42×0.46) means that the area of 1 pixel corresponds to the actual space area of 0.42×0.46 (mm×mm) to eliminate quantitative differences between different individuals.

The risk assessment model 340 is for assessing the cardiovascular disease incidence rate in the subject after 1 to 5 years. The risk assessment model 340 is obtained by integrating the probability of having the epicardial fat 410 or the fat content around heart obtained by the fat identification and quantification model 310 with one of the reference medical record data 220 corresponding, and then training to convergence by a gradient descent algorithm. The gradient descent algorithm can be a XGBoost machine-learning model, a CatBoost machine-learning model or a H2O AutoML ensemble machine-learning model.

In detail, the reference medical record data can include a demographic information, a comorbidity information, a medication information and a biochemical profile. The demographic information can include age, gender, body measurements [e.g., height, weight and body mass index (BMI)], blood pressure [including diastolic blood pressure (DBP) and systolic blood pressure (SBP)], smoking, and alcohol. The comorbidity information can include whether the subject has diabetes, hypertension, obstructive sleep apnea, coronary artery disease, and/or atrial fibrillation. The medication information refers to the medication record of the subject within 1 year from the testing date when the reference medical image (the reference CXR image or the reference CT image sequence) was taken, which can include Aspirin, Dipyridamole, Clopidogrel, Ticagrelor, anti-platelet agent, non-steroidal anti-inflammatory drug, ACEI, α1 blocker, α2 agonist, angiotensin receptor blocker, β blocker, calcium-channel blocker, diuretics, Hydralazine, organic nitrate, insulin, Isosorbide, NTG sublingual tablets, renin inhibitor, oral antidiabetic agent, SLGT-2 inhibitor, GLP-1 agonist, ACEI/ARB, Timolol, Metoprolol, Propranolol, Bisoprolol, and CARVEDILOL®. The biochemical profile can include detection data of glucose, calcium, albumin, uric acid, serum creatinine, hemoglobin, total cholesterol, triglycerides, sodium, potassium, aspartate transaminase (AST), alanine aminotransferase (ALT), high-sensitivity C-reactive protein (hs-CRP), red blood cell count, platelet, white blood cell count, low-density lipoprotein, high-density lipoprotein, creatine kinase, creatine kinase-MB and/or troponin I.

II. Cardiovascular Disease Risk Assessment Method

Figure 6:
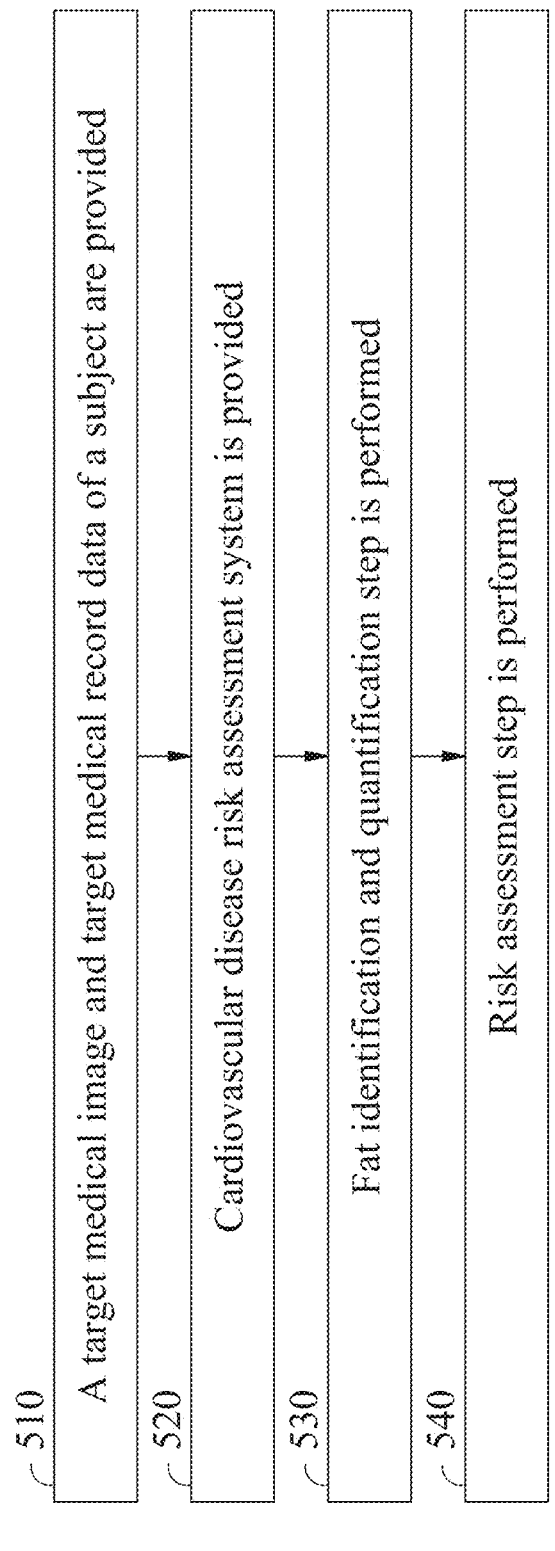
FIG. 6 is a step flow chart of a cardiovascular disease risk assessment method according to another embodiment of the present disclosure.

Reference is made to FIG. 6, which is a step flow chart of a cardiovascular disease risk assessment method 500 according to another embodiment of the present disclosure. The cardiovascular disease risk assessment method 500 includes Step 510, Step 520, Step 530 and Step 540.

In Step 510, a target medical image and a target medical record data are provided, and the target medical image is a target CXR (chest x-ray) image and/or a target CT (computerized tomography) image sequence. The target CT image sequence includes a plurality of target cross-sectional CT images and/or a target sagittal CT image. In Step 520, the aforementioned cardiovascular disease risk assessment system 100 is provided.

In Step 530, a fat identification and quantification step is performed. The CXR image extraction module 320 of the fat identification and quantification model 310 is used to calculate a probability of having the epicardial fat 410 in the target CXR image, and the CT image extraction module 330 of the fat identification and quantification model 310 is used to identify a fat distribution in the target CT image sequence and quantify a fat content around heart in the target CT image sequence.

In Step 540, a risk assessment step is performed. The target medical record data is integrated with the probability of having the epicardial fat 410 or the fat content around heart using the risk assessment model 340 to calculate a cardiovascular disease incidence rate in the subject after 1 to 5 years. The target medical record data can include a demographic information, a comorbidity information, a medication information and a biochemical profile.

III. Example

To evaluate the accuracy of the cardiovascular disease risk assessment system 100 and the cardiovascular disease risk assessment method 500 of the present disclosure in assessing the cardiovascular disease incidence rate in subjects after 1 to 5 years, the cardiovascular disease risk assessment system 100 of the present disclosure was supplemented by the cardiovascular disease risk assessment method 500 of the present disclosure for testing. For the same details, please refer to the previous paragraph and will not be repeated here.

The reference medical images 210 and the reference medical record data 220 used in the present disclosure are from the cardiovascular database collected by the Big Data Center of the China Medical University Hospital. The data covers a total of 88,164 subjects from 2003 to 2020, including 312,288 reference medical images 210 and a total of 3.34 million reference medical record data 220, of which 3,343 subjects were diagnosed with cardiovascular disease within 5 years (corresponding to 9,032 reference medical images 210), and 78,023 subjects had not been diagnosed with cardiovascular disease within 5 years (corresponding to 268,489 reference medical images 210). A total of 277,521 sample groups constitute the data set, which is further divided into 177,614 training sample groups as the training set, 44,403 validation sample groups as the validation set, and 55,504 test sample groups. Each sample group includes a reference CXR posterior-anterior (PA) image, a reference chest CT image sequence, and a reference abdominal CT image sequence.

First, the reference medical images 210 were used to calculate the probability of having the epicardial fat 410 in each of the reference CXR images 211 using the CXR image extraction module 320 in the fat identification and quantification model 310, and the CT image extraction module 330 was used to identify the fat distribution in each of the reference chest CT image sequences and each of the reference abdominal CT image sequences, and to quantify the fat content around heart in each of the reference chest CT image sequences and each of the reference abdominal CT image sequences. Then the medical record data 220 including the demographic information, the comorbidity information, the medication information and the biochemical profile were integrated with the probability of having the epicardial fat 410 or the fat content around heart using the risk assessment model 340 to calculate the cardiovascular disease incidence rate in the subjects after 1 to 5 years.

The test includes the base model, Example 1 and Example 2. The base model was modeled using the same seven index parameters as the Framingham risk score. The Framingham risk is an algorithm used to estimate 10-year cardiovascular risk of an individual, which uses seven selected features including age, gender, total cholesterol, high-density cholesterol, systolic blood pressure, smoking and diabetes to calculate the risk of cardiovascular disease within next 10 years. That is, only the risk assessment model 340 was used in the base model to evaluate the cardiovascular disease incidence rate. In Example 1, the fat identification and quantification model 310 was used to calculate the probability of having the epicardial fat 410 in the reference medical image 210, and then the risk assessment model 340 was used to evaluate the cardiovascular disease incidence rate. In Example 2, the fat identification and quantification model 310 was used to quantify the fat content around heart in the reference medical image 210, and then the risk assessment model 340 was used to evaluate the cardiovascular disease incidence rate. The selected features of the reference medical record data 220 used in Example 1 and Example 2 are as shown in Table 1.

TABLE 1

| Data dimensions | Selected features |
| --- | --- |
| Demographic information | Age, gender, systolic blood pressure, body measurement, and smoking |
| Comorbidity information | Diabetes, hypertension, obstructive sleep apnea, and atrial fibrillation |
| Medication information | Non-steroidal anti-inflammatory drug, anti-platelet agent, angiotensin receptor blocker, SLGT-2 inhibitor, GLP-1 agonist, ACEI/ARB, Timolol, Metoprolol, Propranolol, Bisoprolol, and CARVEDILOL ® |
| Biochemical profile | Glucose, serum creatinine, hemoglobin, potassium, sodium, aspartate transaminase, alanine aminotransferase, high-sensitivity C-reactive protein, red blood cell count, platelet, and white blood cell count |

After combining the above three different features, the gradient descent algorithm was used to train the machine learning model, and the performance of the base model, Example 1 and Example 2 was evaluated through multiple indicators. Please refer to Table 2, which shows the performance of the base model, Example 1 and Example 2 evaluated by accuracy, sensitivity, specificity, negative predictive value (NPV), correct rate, and area under curve (AUC).

TABLE 2

| Cardiovascular disease | Base model | | | Example 1 | | | Example 2 | | |
|---|---|---|---|---|---|---|---|---|---|
| features assessment | train | val | test | train | val | test | train | val | test |
| Accuracy | 15% | 4% | 6% | 27% | 10% | 11% | 23% | 10% | 10% |
| Sensitivity | 95% | 44% | 44% | 100% | 44% | 44% | 98% | 44% | 44% |
| Specificity | 80% | 77% | 79% | 90% | 91% | 89% | 88% | 91% | 88% |
| NPV | 100% | 98% | 98% | 100% | 99% | 98% | 100% | 99% | 98% |
| Correct rate | 81% | 76% | 78% | 90% | 90% | 87% | 89% | 90% | 87% |
| AUC | 95% | 64% | 65% | 98% | 70% | 68% | 98% | 71% | 70% |

The results in Table 2 show that accuracy of the base model is 6%, while accuracy of both Example 1 and Example 2 can be improved to ≥10%. The base model, Example 1 and Example 2 all showed good performance in terms of specificity and NPV, with NPV reaching over 98%. However, compared with the base model, correct rate of Example 1 and Example 2 can both reach 87%, and AUC of Example 1 and Example 2 can reach 68% and 70%, respectively.

In summary, the cardiovascular disease risk assessment system and the cardiovascular disease risk assessment method of the present disclosure can assist in calculating the probability of having the epicardial fat of the subject, identifying the fat distribution of the subject and quantifying the fat content around heart of the subject through the target medical image including the target CXR image and the target CT image sequence. Then the target medical record data is integrated with the probability of having the epicardial fat or the fat content around heart obtained to estimate the cardiovascular disease incidence rate in the subject after 1 to 5 years. When the subject undergoes CXR angiography or CT scan, the cardiovascular disease risk assessment system and the cardiovascular disease risk assessment method of the present disclosure can assist in analyzing the subject's physical condition and potential risk of cardiovascular disease to provide clinicians with a basis for decision-making, and has excellent clinical application potential.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A cardiovascular disease risk assessment system, comprising:
  a storage storing a plurality of reference medical images and a plurality of reference medical record data, and each of the plurality of reference medical images corresponding to one of the plurality of reference medical record data, wherein each of the plurality of reference medical images is a reference CXR image and/or a reference CT image sequence, and the reference CT image sequence includes a plurality of reference cross-sectional CT images and/or a reference sagittal CT image; and a processor signally connected to the storage and storing a program, wherein the program estimates a cardiovascular disease incidence rate of a subject when the program is executed by the processor, and the program comprises:
    a fat identification and quantification model for calculating a probability of having an epicardial fat in each of the plurality of reference medical images or identifying a fat distribution and quantifying a fat content around heart in each of the plurality of reference medical images, wherein the fat identification and quantification model comprises:
      a CXR image extraction module for calculating the probability of having the epicardial fat in each of the plurality of reference CXR images, wherein the CXR image extraction module is obtained by labelling each of the plurality of reference CXR images and then integrating with one of the plurality of reference medical record data corresponding, and then training to convergence by a two-dimensional CNN convolutional neural network learning classifier; and
      a CT image extraction module for identifying the fat distribution and quantifying the fat content around heart in each of the plurality of reference CT image sequences, wherein the CT image extraction module identifies and segments an organ and a tissue in each of the plurality of reference CT image sequences by a three-dimensional U-net convolutional neural network classifier to obtain a plurality of reference segmented CT images, and analyzes a Hounsfield unit in each of the plurality of reference CT image sequences to obtain a plurality of fat contents by a feature model; and
    a risk assessment model for assessing the cardiovascular disease incidence rate in the subject after 1 to 5 years, wherein the risk assessment model is obtained by integrating the probability of having the epicardial fat or the fat content around heart obtained by the fat identification and quantification model with one of the plurality of reference medical record data corresponding, and then training to convergence by a gradient descent algorithm.

2. The cardiovascular disease risk assessment system of claim 1, wherein the CXR image extraction module comprises:
  a cardiothoracic ratio assessment unit for identifying and segmenting a lung lobe contour and a heart contour in each of the plurality of reference CXR images to output a plurality of reference segmented CXR images;

a feature extraction unit for detecting and locating an edge, a texture and a shape of a heart and the epicardial fat in each of the plurality of reference segmented CXR images to output a plurality of reference labeled CXR images; and a calculation unit for calculating the probability of having the epicardial fat in each of the plurality of reference labeled CXR images.

3. The cardiovascular disease risk assessment system of claim 2, wherein the CXR image extraction module further comprises a cropping unit for removing unnecessary image ranges around the heart and a lung lobe in the plurality of reference segmented CXR images to obtain a plurality of reference cropped segmented CXR images.

4. The cardiovascular disease risk assessment system of claim 1, wherein the CT image extraction module comprises:

a vertebra positioning unit for stacking the plurality of reference cross-sectional CT images in each of the plurality of reference CT image sequences into a three-dimensional space to output a plurality of reference three-dimensional CT images, and distinguishing a vertebra position in each of the plurality of reference three-dimensional CT images;

an organ recognition unit for segmenting the organ and the tissue in each of the plurality of reference three-dimensional CT images to output a plurality of reference segmented CT images;

a tissue distribution analysis unit for analyzing the Hounsfield unit in each of the plurality of reference CT image sequences to obtain a tissue distribution in each of the plurality of reference CT image sequences, and measuring the plurality of fat contents in each of the plurality of reference CT image sequences; and a quantification unit for quantifying the plurality of fat contents in each of the plurality of reference CT image sequences and one of the reference segmented CT images corresponding with a fat profile index to obtain the fat content around heart.

5. The cardiovascular disease risk assessment system of claim 4, wherein the plurality of fat contents comprise an epicardial fat content, a fat content around heart and a visceral fat content.

6. The cardiovascular disease risk assessment system of claim 4, wherein the fat profile index comprises a fat/heart ratio quartile, a fat/heart ratio, and an actual fat size restoration.

7. The cardiovascular disease risk assessment system of claim 1, wherein each of the plurality of reference medical record data includes a demographic information, a comorbidity information, a medication information and a biochemical profile.

8. The cardiovascular disease risk assessment system of claim 1, wherein the gradient descent algorithm is a XGBoost machine-learning model, a CatBoost machine-learning model or a H2O AutoML ensemble machine-learning model.

9. A cardiovascular disease risk assessment method, comprising:

providing a target medical image and a target medical record data of a subject, wherein the target medical image is a target CXR image and/or a target CT image sequence;

providing the cardiovascular disease risk assessment system of claim 1;

performing a fat identification and quantification step, wherein the CXR image extraction module of the fat identification and quantification model is used to calculate a probability of having an epicardial fat in the target CXR image, and the CT image extraction module of the fat identification and quantification model is used to identify a fat distribution in the target CT image sequence and quantify a fat content around heart in the target CT image sequence; and performing a risk assessment step, wherein the target medical record data is integrated with the probability of having the epicardial fat or the fat content around heart using the risk assessment model to calculate a cardiovascular disease incidence rate in the subject after 1 to 5 years.

10. The cardiovascular disease risk assessment method of claim 9, wherein the target medical record data comprises a demographic information, a comorbidity information, a medication information and a biochemical profile.

* * * * *